United States Patent
Sias et al.

(10) Patent No.: US 12,357,717 B2
(45) Date of Patent: Jul. 15, 2025

(54) STERILIZATION SYSTEMS AND METHODS

(71) Applicants: Ralph M. Sias, Oceanside, CA (US); Bradley H. Buchanan, Eastsound, WA (US); Therese M. Stewart, Wellington, FL (US)

(72) Inventors: Ralph M. Sias, Oceanside, CA (US); Bradley H. Buchanan, Eastsound, WA (US); Therese M. Stewart, Wellington, FL (US)

(73) Assignee: Sterile Solutions International, Inc., Wellington, FL (US)

( * ) Notice: Subject to any disclaimer, the term of this patent is extended or adjusted under 35 U.S.C. 154(b) by 426 days.

(21) Appl. No.: 17/751,443

(22) Filed: May 23, 2022

(65) Prior Publication Data

US 2022/0378962 A1 Dec. 1, 2022

Related U.S. Application Data

(60) Provisional application No. 63/207,770, filed on Mar. 22, 2021.

(51) Int. Cl.
*A61L 2/20* (2006.01)
*A61L 2/14* (2006.01)

(52) U.S. Cl.
CPC ............ *A61L 2/208* (2013.01); *A61L 2/14* (2013.01); *A61L 2202/122* (2013.01); *A61L 2202/14* (2013.01); *A61L 2202/24* (2013.01)

(58) Field of Classification Search
CPC ...... A61L 2/208; A61L 2/14; A61L 2202/122; A61L 2202/14; A61L 2202/24; A61L 2202/11; A61L 2/20
See application file for complete search history.

(56) References Cited

U.S. PATENT DOCUMENTS

| | | | | |
|---|---|---|---|---|
| 5,667,753 A | * | 9/1997 | Jacobs | C01B 15/037 422/23 |
| 6,066,294 A | * | 5/2000 | Lin | A61L 2/186 134/183 |
| 8,071,081 B2 | * | 12/2011 | Weiss | A61L 9/015 424/617 |
| 8,382,008 B1 | * | 2/2013 | Ricciardi | G05B 15/02 239/338 |
| 2003/0147775 A1 | * | 8/2003 | Lin | A61L 2/208 422/33 |
| 2011/0233142 A1 | * | 9/2011 | Grossman | C02F 9/20 210/175 |
| 2012/0055513 A1 | * | 3/2012 | Eglmeier | A61L 9/205 134/104.1 |

* cited by examiner

*Primary Examiner* — Regina M Yoo
(74) *Attorney, Agent, or Firm* — David Meibos; Maywood IP Law

(57) ABSTRACT

A sterilization system for sterilizing an article is disclosed. The sterilization system may include a hydrogen peroxide generation system configured to generate hydrogen peroxide, a hydroxyl generation system configured to produce a flow of hydroxyl radicals that causes deterioration of the hydrogen peroxide to produce hydroxyl ions, and a sterilization chamber configured to expose the article to the hydroxyl ions to sterilize the article. Additionally, methods for sterilizing articles are disclosed. Those methods may include generating hydrogen peroxide, producing a flow of hydroxyl radicals that causes deterioration of the hydrogen peroxide to produce hydroxyl ions, and exposing the article to the hydroxyl ions to sterilize the article.

5 Claims, 4 Drawing Sheets

| Microorganism | Sterilization Process | Dose | Exposure Time | Results |
|---|---|---|---|---|
| Serratia marcescens | UV (254 nm) | 300 mJ/cm² | 5 min | Complete kill |
| Serratia marcescens | H2O2 gas | 2500 ppm | 5 min | Complete kill |
| Serratia marcescens | Proprietary Process | TBD | < 3 min | Complete kill |
| Bacillus subtilis | UV (254 nm) | 600 mJ/cm² | 10 min | Partial kill |
| Bacillus subtilis | H2O2 gas | 2500 ppm | 5 min | Complete kill |
| Bacillus subtilis | Proprietary Process | TBD | < 3 min | Complete kill |
| Geobacillus stearothermophilus | UV (254 nm) | 600 mJ/cm² | 10 min | Partial kill |
| Geobacillus stearothermophilus | H2O2 gas | 2500 ppm | 5 min | Complete kill |
| Geobacillus stearothermophilus | Proprietary Process | TBD | < 3 min | Complete kill |

*Fig. 3*

STERILIZATION SYSTEMS AND METHODS

CROSS-REFERENCE TO RELATED APPLICATIONS

The present application claims the benefit of U.S. Provisional Patent Application Ser. No. 63/207,770, entitled PHOTO-CATALYTIC CONTROLLED DECOMPOSITION OF H2O2 FOR DECONTAMINATION AND STERILIZATION, which was filed on Mar. 22, 2021. The above application is incorporated by reference herein as though set forth in its entirety.

TECHNICAL FIELD

The present disclosure relates to systems and methods for sterilization and/or sanitation of articles. More precisely, the present disclosure relates to sterilization through the use of hydrogen peroxide.

BACKGROUND

Sterilization is a process that destroys or eliminates microbial life. It may be carried out by physical and/or chemical methods. Every day, hospitals and other health care facilities perform various surgical procedures that require invasive access to patient tissue. The medical device or the surgical instrument that contacts the patient's internal tissues may beneficially be sterilized prior to use to reduce the risk of introducing pathogens into the patient. Several outbreaks and infections have been reported in healthcare facilities, due to improper sterilization of devices used in surgical procedures. Therefore, enhanced decontamination techniques for medical and surgical devices are needed.

SUMMARY

In order to decontaminate or sterilize an article, the article may be treated with hydroxyl ions. Hydroxyl ions may be produced through the decomposition of hydrogen peroxide. According to some embodiments, sterilization is accomplished by producing gaseous hydrogen peroxide in a hydrogen peroxide generation system. The gaseous hydrogen peroxide may be deteriorated by a flow of hydroxyl radicals to produce hydroxyl ions. The hydroxyl ions may be transported to a local or remote sterilization chamber containing an article to be sterilized.

According to one embodiment, a sterilization system for sterilizing an article may include a hydrogen peroxide generation system configured to generate hydrogen peroxide, a hydroxyl generation system configured to produce a flow of hydroxyl radicals that causes deterioration of the hydrogen peroxide to produce hydroxyl ions, and a sterilization chamber configured to expose the article to the hydroxyl ions to sterilize the article.

The sterilization system may further have a temperature regulation system configured to maintain a temperature of the sterilization chamber between about fifty-five degrees Celsius and about sixty-five degrees Celsius.

The sterilization system may further have a gas movement system configured to move the hydrogen peroxide from the hydrogen peroxide generation system to the hydroxyl generation system and into the sterilization chamber.

The gas movement system may further be configured to move the hydrogen peroxide via a gas that is non-reactive with the hydrogen peroxide, the hydroxyl radicals, and the hydroxyl ions.

The gas may be predominantly composed of nitrogen.

The hydrogen peroxide generation system may include a hydrogen peroxide generation chamber configured to hold a peroxide complex, and a heating element configured to heat the peroxide complex in the hydrogen peroxide generation chamber to release peroxide gas.

The hydroxyl generation system may include a hydroxyl radical source, and a UV light source configured to bombard the hydroxyl radical source with UV light to release the flow of hydroxyl radicals.

The hydroxyl radical source may be predominantly composed of titanium dioxide.

The wavelength of the UV light source may be between about 250 nm and about 280 nm.

The sterilization chamber may be remote from the hydroxyl generation system.

According to one embodiment, a method for sterilizing an article may include generating hydrogen peroxide, producing a flow of hydroxyl radicals that causes deterioration of the hydrogen peroxide to produce hydroxyl ions, and exposing the article to the hydroxyl ions to sterilize the article.

The method may further include, while exposing the article to the hydroxyl ions, maintaining an environment surrounding the article at a temperature between about fifty-five degrees Celsius and about sixty-five degrees Celsius.

The method may further include using a gas to move the hydrogen peroxide to the flow of hydroxyl radicals and to the article.

The gas may be non-reactive with the hydrogen peroxide, the hydroxyl radicals, and the hydroxyl ions.

The gas may be predominantly composed of nitrogen.

Generating the hydrogen peroxide may include heating a peroxide complex in a chamber to release peroxide gas.

Producing the flow of hydroxyl radicals may include bombarding a hydroxyl radical source with UV light to release the flow of hydroxyl radicals.

The hydroxyl radical source may be predominantly composed of titanium dioxide.

Exposing the article to the hydroxyl ions may be carried out remotely from the flow of hydroxyl radicals. The method may further include, prior to exposing the article to the hydroxyl ions, transporting the hydroxyl ions to the article.

According to one embodiment, a sterilization system for sterilizing an article may include a hydrogen peroxide generation chamber that holds a peroxide complex, a heating element configured to heat the peroxide complex to generate hydrogen peroxide, a hydroxyl radical source, a UV light configured to bombard the hydroxyl radical source with UV light to release a flow of hydroxyl radicals, a gas movement system configured to move the hydrogen peroxide from the hydrogen peroxide generation chamber to the flow of hydroxyl radicals such that the flow of hydroxyl radicals causes deterioration of the hydrogen peroxide to produce hydroxyl ions, and a sterilization chamber configured to expose the article to the hydroxyl ions to sterilize the article.

These and other features and advantages of the present disclosure will become more fully apparent from the following description and appended claims or may be learned by the practice of the devices, systems, and methods set forth hereinafter.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIG. 3 is a table showing the time and results obtained with the sterilization system of FIG. 2, compared against the results obtained via application of UV light and hydrogen peroxide.

Figure 1:
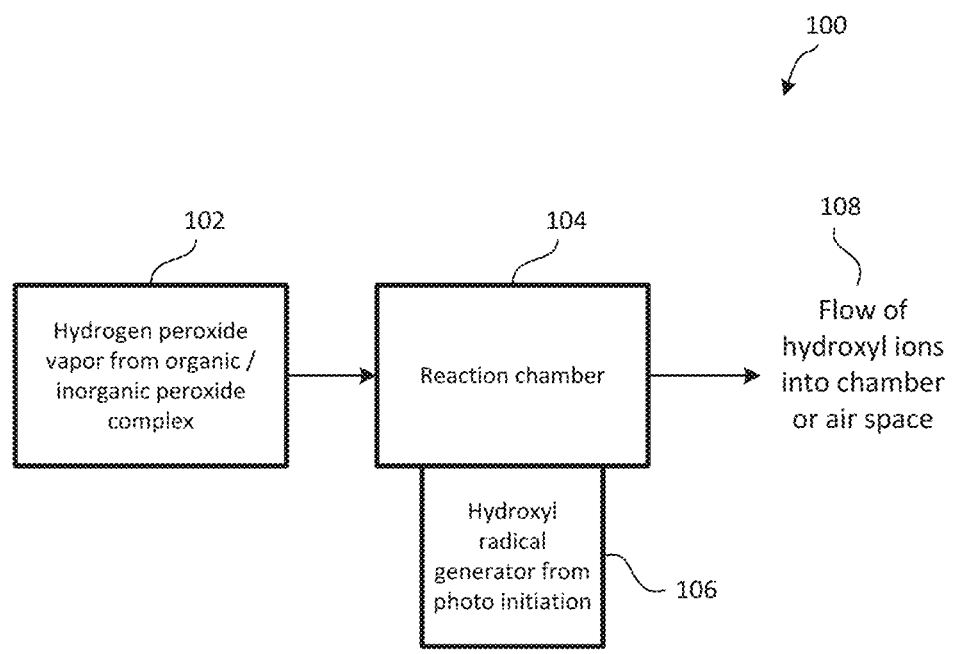
FIG. 1 is a flow diagram of a sterilization process according to one embodiment.

It is to be understood that the drawings are for purposes of illustrating the concepts of the disclosure and are not to scale. Furthermore, the drawings illustrate exemplary embodiments and do not represent limitations to the scope of the disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, systems, and methods, as represented in the Figures, is not intended to limit the scope of the disclosure, as claimed, but is merely representative of exemplary embodiments of the disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

What makes hydrogen peroxide a superior sterilization agent is its "unbalanced" molecular composition. Since hydrogen peroxide is a water molecule with an added oxygen atom, it is unstable and seeks to decompose into its stable components (water and oxygen). It essentially decomposes in the following order:

$$2[H_2O_2] \rightarrow 4[OH-] \rightarrow 2[H_2O] + O_2$$

While there are other transition components during decomposition (H++HO$_2$- etc.) the ones which affect sterilization are the hydroxide ions, i.e. OH—. These are commonly referred to as hydroxyls or hydroxyl ions when they are not part of a larger molecule.

OH- ions are different from the OH radical. The OH- ion is reactive because of its negative charge and ionically bonds to other molecules. The OH radical is charge neutral but has an unpaired electron spin configuration and makes it very unstable. Because of its high degree of instability, the radical is very short lived and is only present for fractions of a second.

Because of their negative charge, the hydroxyl ions create oxidation/reduction (redox) reactions with organic molecules such as microorganisms and many chemical contaminants:

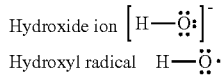

Hydroxide ion $[H—\ddot{O}:]^-$

Hydroxyl radical $H—\ddot{O}\cdot$

The redox reaction kills microorganisms by lysing (rupturing) the cell walls. Further, this reaction may be effective for removing and/or deactivating chemical contaminants by changing their molecular structure.

The effectiveness of hydrogen peroxide for sterilization or high-level disinfection may be enhanced by controlling the rate of H$_2$O$_2$ decomposition. The rate should be such that OH- ions are produced at a sufficient quantity for a sufficient time to reach the contaminating microorganisms. Sterility is usually defined as a 6 log 10 reduction (99.9999%) of endospores while high level decontamination requires a 6 log 10 reduction of Mycobacteria.

The decomposition rate of hydrogen peroxide may be difficult to control due to the effects of hydrogen bonding between water and hydrogen peroxide molecules and the reactivity of the hydroxyl ions. The hydrogen bonding tends to keep the hydrogen peroxide bound in the aqueous solution until a reaction causes an avalanche of decomposition. Reaction rates tend to be very slow (no catalyst involved) or very fast (with the addition of a catalyst).

A good example of different rates of decomposition is the reaction seen when a 3% hydrogen peroxide solution is poured onto an open wound. The hydrogen peroxide stays bound with the water until it contacts open bonding sites, primarily catalase & glutathione in the wound. Upon contact, virtually all of the hydrogen peroxide decomposes rapidly as seen in the foaming within the wound. The decomposition is so fast and intense that the reacting OH- ions kill microorganisms and tissue.

There are several products currently on the market that utilize a type of hydrogen peroxide sterilization of medical instruments. Each of these products has limitations that make them less than ideal. A first product, distributed by J&J, controls the rate of H$_2$O$_2$ decomposition by pulling a high vacuum in a chamber (creating a water free environment), injecting aqueous hydrogen peroxide (30% H$_2$O$_2$), and charging the resulting vapor with high power RF (microwave) to create a plasma. The OH- ions are created quickly and maintained by the plasma until the cycle is complete. Additionally, OH radicals are present in transitional states while the plasma is present. The J&J system provides effective sterilization but is expensive and complex due to the need for the vacuum tank, pumps, RF generator, impedance matching network, etc. It is also slow because of the time required to pull the vacuum.

A second product, distributed by Steris, controls the rate by drying the air in an enclosure prior to flashing aqueous hydrogen peroxide (around 30%) off a hot surface into the dry air. There is no external energy applied to create decomposition, therefore the rate is controlled by temperature, constant water content, and the constant addition of new $H_2O_2$. The system is very slow because of the time required to dry the air and the highly variable density of OH– ions available during the cycle.

Another product distributed by Bioquell applies an aerosol (or fog) of 30% $H_2O_2$ to a sealed volume (i.e. a room or chamber). The aerosol moistens the surfaces within the volume with the $H_2O_2$ solution which allows the OH– ions to be released from the water when bonding sites are available. After a suitable dwell time, the moistened surfaces are neutralized and dried, and the room is vented. The Bioquell system is slow and wet and requires manpower to physically seal a room prior to treatment. Initial humidity in the room affects the length of the process which makes each cycle variable.

Each of these products has limitations as to the practicality and the effectiveness of the process. One common feature of all of these products is the use of aqueous hydrogen peroxide. Aqueous solutions of hydrogen peroxide have limitations on their use in sterilization. One of the issues with aqueous solutions or with having water of any kind in the application is that water condenses at a lower temperature than hydrogen peroxide. Because of this, a barrier of water is often present on the surfaces to be sterilized. To reach the microorganisms and chemical contaminants, the hydrogen peroxide must diffuse through the water condensed on the surface to deactivate or destroy the contaminants. Diffusion is a slow process. Additionally, chemical reactions occur between the water and the hydrogen peroxide, limiting the amount of hydrogen peroxide available for sterilization.

The present disclosure provides many benefits over these known methods. In some embodiments, a peroxide complex, rather than an aqueous solution, may be used to generate hydrogen peroxide, avoiding the creation of a water barrier on the surfaces to be sterilized. Relatively simple and/or inexpensive components may be used to generate hydroxyl ions that can be used for rapid sterilization.

FIG. 1 is a flow diagram of a sterilization process 100 according to one embodiment. Hydrogen peroxide gas may be produced through the use of a peroxide complex 102. The gaseous hydrogen peroxide may be transported into a reaction chamber 104. In the reaction chamber 104, hydroxyl radicals produced by a hydroxyl radical generator 106 may react with the hydrogen peroxide to produce a flow of hydroxyl ions 108. The hydroxyl ions may be produced in the hydroxyl radical generator 106 by photo initiation. Once the hydrogen peroxide has been decomposed by the hydroxyl radicals into the flow of hydroxyl ions 108, the hydroxyl ions may be transported to a sterilization chamber or other sterilization area, at which the hydroxyl ions may react with microorganisms and chemical contaminants to deactivate and/or destroy them as described above.

Figure 2:
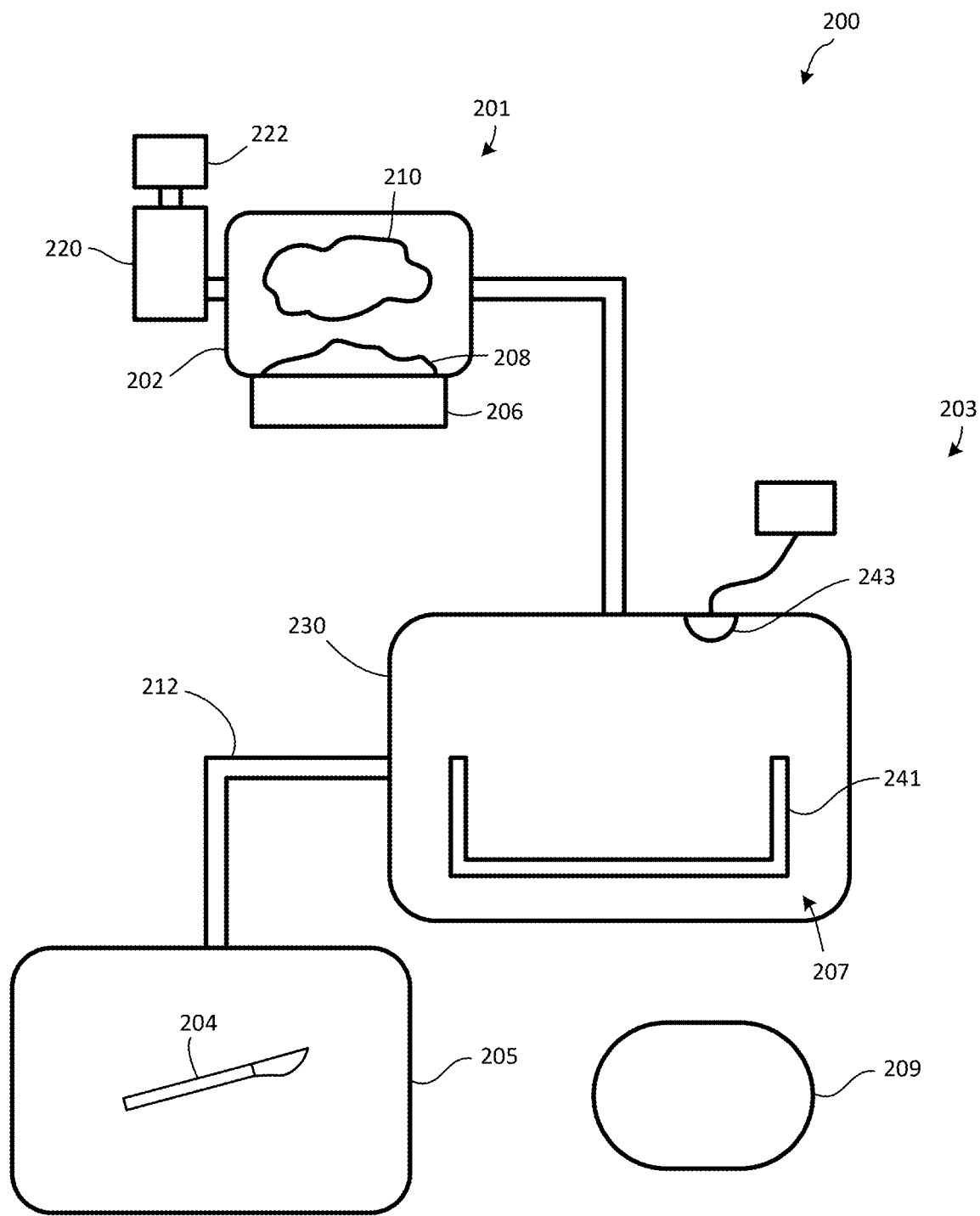
FIG. 2 is a schematic view of a sterilization system that implements the sterilization process of FIG. 1, according to one embodiment.

FIG. 2 is a schematic diagram of a sterilization system 200 according to one embodiment. The sterilization system 200 may include a hydrogen peroxide generation system 201, a reaction system 203, and a sterilization chamber 205 containing an article 204 to be sterilized.

The hydrogen peroxide generation system 201 may include a chamber 202 and a heating element 206. A peroxide complex 208 may be placed in the chamber. The peroxide complex may optionally be placed directly on the heating element 206, or on an interior wall of the chamber 202 adjacent to the heating element 206. Peroxide compounds are chemical compounds that have hydrogen peroxide bonded to another compound. The hydrogen peroxide can be dissociated from the other compound by heat and/or chemical reactions. The peroxide complex may be organic or inorganic. Some examples of peroxide complexes include carbamide peroxide, also known as urea peroxide. Carbamide peroxide has a chemical composition of $CH_6N_2O_3$ and a molecular weight of 94.07 g/mol. Hydrogen peroxide has a chemical composition of $H_2O_2$ and a molecular weight of 34.0147 g/mol. As the carbamide peroxide decomposes, 36.1% of the weight of the carbamide is hydrogen peroxide. To create 1 mol of hydrogen peroxide requires 94.59 g of carbamide peroxide. Said another way, the ratio of hydrogen peroxide in carbamide peroxide is 1:3, or the hydrogen peroxide is one third the weight of the carbamide peroxide.

The peroxide complex may be heated in the chamber 202 with the heating element 206. This may release hydrogen peroxide gas from the peroxide complex 208. The hydrogen E peroxide gas 210 may be transported to the reaction system 203. The heating element 206 may be used to provide the optimal flow rate of hydrogen peroxide. In some embodiments, the heating element 206 may be designed to heat the peroxide complex 208 to a temperature within the range of 0° C. to 100° C. More precisely, the heating element 206 may be designed to heat the peroxide complex 208 to a temperature within the range of 30° C. to 80° C. Yet more precisely, heating element 206 may be designed to heat the peroxide complex 208 to a temperature within the range of 50° C. to 70° C. Still more precisely, the heating element 206 may be designed to heat the peroxide complex 208 to a temperature within the range of 55° C. to 65° C. Even more precisely, the heating element 206 may be designed to heat the peroxide complex 208 to a temperature of about 60° C.

In some embodiments, a thermostat (not shown) within the chamber 202 may be used to control the heating element 206 to keep the peroxide complex 208 within the desired temperature range. Further, in some embodiments, the heating element 206 may be used to control the rate of hydrogen peroxide generation, for example, by heating the peroxide complex 208 to a higher temperature to increase the rate of hydrogen peroxide generation, or allowing reduction in the temperature of the peroxide complex 208 to slow the rate of hydrogen peroxide generation.

In some embodiments, the hydrogen peroxide gas is transported by a gas transport system 220. In some embodiments, the gas transport system 220 utilizes ambient air to move gases throughout the system. The ambient air may be sucked into the gas transport system 220 and urged into the chamber 202 under pressure to move the hydrogen peroxide gas 210 out of the chamber 202, to the reaction system 203. Ambient air may be acceptable as a transport gas. However, ambient air has a limitation in that oxygen is a part of ambient air, and may react with the hydrogen peroxide gas 210 and thus limit the amount of hydrogen peroxide gas 210 available in the reaction system 203. Additionally, ambient air often contains water vapor. As explained above, water vapor is highly reactive with hydrogen peroxide and limits the amount of hydrogen peroxide gas 210 available as well as limiting the reaction surface of the hydrogen peroxide.

One of the reasons that the inventors have developed an anhydrous hydrogen peroxide sterilization system is that hydrogen peroxide in solution in water tends to react much more slowly. Even with gaseous hydrogen peroxide and water, the water condenses first, and may form a barrier on the surfaces which are being sterilized, as described above. The hydrogen peroxide may still reach the surface, but it must diffuse through the water, slowing the reaction and reducing the available amount of hydrogen peroxide. Therefore, an ambient air gas transport system is usable in some conditions but can be a limiting factor in the effectiveness of the sterilization system 200.

In some embodiments, a transport system utilizes a sealed gas in place of ambient air. The sealed gas may be housed in a cannister 222 that attached to the gas transport system 220. Utilizing a gas that is non-reactive with hydrogen peroxide and with reactive oxygen species may be advantageous. Non-reactive gases include but are not limited to nitrogen and argon. The non-reactive gas may be pressurized by the gas transport system 220 and used to move the hydrogen peroxide gas 210 to the reaction system 203. The non-reactive gases may optionally be recaptured from the reaction system 203 and reused by the gas transport system 220.

In some embodiments, the non-reactive gas may be pure nitrogen. In alternative embodiments, the non-reactive gas may include other trace elements, for example, at a concentration of less than 20%, less than 15%, less than 10%, or less than 5% of the volume of the gas.

The reaction system 203 may include a reaction chamber 230. A hydroxyl radical generation system 207 may also be connected to the reaction chamber 230. In some embodiments, the hydroxyl radical generation system 207 is housed within the reaction chamber 230. The hydroxyl radical generation system 207 may include a UV light source 243 and a hydroxyl radical source such as a photo initiator. UV light from the UV light source 243 may react with the photo initiator to produce hydroxyl radicals.

Photo initiators include, but are not limited to, transition metal oxides, which are compounds composed of oxygen atoms bound to transition metals. Transition metal oxides are commonly used for their catalytic properties. The versatility of these molecules also leads to their used as pigments in paints and plastics. Transition metal oxides include; titanium dioxide ($TiO_2$), strontium dioxide ($SrO_2$), Zirconium dioxide ($ZrO_2$), Zinc oxide ($ZnO$), Copper oxide ($CuO$), and others. Metal ions such as Copper ($Cu+$) are also used as photo initiators. Combinations of metal oxides with each other or with other compounds can also be strong photo initiators. Titanium dioxide is one of the most used photo initiators. It is generally safe to work with, is readily available, and is an efficient photo initiator.

Thus, in FIG. 2, the photo initiator 241 may take the form of a plate composed of titanium dioxide. The plate may be shaped to provide an extended surface area that receives the UV light from the UV light source 243, thus, enhancing the rate of hydroxyl radical production. In alternative embodiments, the photo initiator 241 is a screen to which titanium dioxide is attached.

The titanium dioxide can be attached to the screen in a variety of ways. The titanium dioxide may be a coating applied to a substrate, such as paint or powder coating. The substrate may be metal, such as copper, iron, zinc, stainless steel, or other metals. Alternatively, the substrate may be a polymer such as plastic. The titanium dioxide may be manufactured into the screen itself such as by being an ingredient in a polymer used to form the screen. In embodiments in which the titanium dioxide is an ingredient in the polymer used to form a screen, the screen may be produced by any polymer fabrication method, including but not limited to extrusion, molding, or by an additive manufacturing method such as 3D printing.

UV light in the wavelengths of 250 nm to 450 nm are known to be effective for photoinitiation. UV light in the wavelengths of 100 nm to 280 nm, otherwise known as UVC, are known to be effective for deactivating and destroying microorganisms such as viruses and bacteria. For use in a sterilization system, a UV light source that produces UV light in a wavelength of between 250 nm and 280 nm would be most beneficial. The UV light may activate titanium dioxide and may have the added benefit of inactivating viruses and bacteria. There are many UV light sources which produce UV light with wavelengths within the range from 250 nm to 280 nm, any of which would be effective for use in the sterilization system 200. In one embodiment, the system uses a UV light source with wavelength of 254 nm.

In the reaction chamber 230, the hydroxyl radicals may mix with the hydrogen peroxide gas 210 to produce hydroxyl ions. The reaction of hydroxyl ions with hydrogen peroxide gas may be a cascading reaction—as the hydrogen peroxide and hydroxyl radicals decompose to hydroxyl ions, the reaction may tend to avalanche. The rate at which the hydroxyl radicals come in contact with the hydrogen peroxide gas 210 may determine the amount of the hydroxyl ions that is produced. The amount of hydroxyl radicals is dependent on the UV light bombarding the photo initiator 241 to release the hydroxyl radicals. The flow of radicals can be increased by turning the UV light source 243 on and/or increasing its intensity. Similarly, the flow of radicals can be reduced by turning the UV light source 243 off and/or reducing its intensity. Additionally or alternatively, the wavelength of UV light emitted by the UV light source 243 may be adjusted to control the reaction. Additionally, in some embodiments, there are multiple UV light sources. By using multiple UV light sources, differing rates of hydroxyl ion production can be maintained through any of the techniques mentioned above, applied to one or multiple of the UV lights. The rate of continuous production of hydroxyl ions from the interaction between hydrogen peroxide gas and hydroxyl radicals can be regulated from the amount of UV light bombarding the titanium dioxide photo initiator.

In some embodiments, the product produced by the hydrogen peroxide generation system and the interaction of the hydrogen peroxide gas with the hydroxyl ions in the hydroxyl generation system may be predominantly hydroxyl ions; however, hydrogen peroxide and hydroxyl radicals may still be present, as the entire volume of the hydrogen peroxide gas may not decompose to hydroxyl ions.

In addition to being reactive with compounds in ambient air, the components of the sterilization product may be reactive with the material of which the generation system, reaction system, and sterilization chamber are composed. These materials may include some metals, such as copper, magnesium, and brass as well as some polymers, including acetal, nitrile, rubber, various synthetic rubbers, and other polymers. Materials that may be non-reactive with the sterilization components may include stainless steel, aluminum, polycarbonate, and polytetrafluoroethylene (PTFE). Therefore, careful design may be required to create the apparatus necessary to generate the reaction and sterilization products.

Once hydroxyl ions have been produced, they may be conveyed to the sterilization chamber 205. In embodiments where the sterilization chamber 205 and the reaction chamber 230 are not the same chamber, the hydroxyl ions may be conveyed from the reaction chamber 230 to the sterilization chamber 205 through a conduit, such as conduit 212. This movement from the reaction chamber 230 to the sterilization chamber 205 may be executed by a transport system, for example, via the ambient air or non-reactive gas that is pressurized by the gas transport system 220. In the alternative, a different conveyance mechanism may be used to convey the hydroxyl ions to the sterilization chamber. For example, a different gas transport system (not shown) may be used. The conduit 212 may be of any length necessary to connect the reaction chamber 230 to the sterilization chamber 205. In some embodiments, the reaction chamber 230 and the sterilization chamber 205 may be located close to one another, such as in the same room. In these embodiments, the conduit 212 is short due to the physical proximity of the reaction chamber and the sterilization chamber 205.

In some embodiments, the sterilization chamber 205 may be in a location that is remote from the location of the remainder of the sterilization system 200, including the hydrogen peroxide generation system 201 and the reaction system 203. In some embodiments, the hydroxyl ions may be generated at an ion production location, and then transported to a separate location (such as a patient care room), and there introduced into the sterilization chamber 205 to sterilize the article 204. Examples of this may include having a generation system and a reaction system in a designated location within a patient care facility, such as a surgery ward, and having sterilization chambers at strategic locations throughout the patient care facility, such as in each surgery room. Another example could be a dentist office, at which the generation and reaction systems are centrally located and the sterilization chambers are in each of the examination rooms. In such cases, the conduit 212 used to transport the hydroxyl ions from the reaction system 203 to the sterilization chamber 205 may be sufficiently long to reach from the reaction chamber to the sterilization chamber.

In some embodiments, the hydroxyl ions are used to sterilize apparatus used to fill vessels, such as vessel 209, used for transporting biological substances such as growth media. The sanitization system may also sterilize at least a portion of the vessel 209 itself. These vessels may be transported to a location removed from the hydrogen peroxide generation system 201 and the hydroxyl radical generation system (the reaction system 203 of FIG. 2). An exemplary filling system, or filling system 400, is shown and described in connection with FIG. 4.

In other embodiments, sterilization may be carried out directly in the reaction chamber 230. Thus, the sterilization chamber 205 of FIG. 2 may be omitted, and the article 204 may be placed directly in the reaction chamber 230 so that it will be sterilized by the hydroxyl ions produced within the reaction chamber 230. This may enable the article 204 to be bombarded by the UV light produced by the UV light source 243, in addition to the effect of the hydroxyl ions generated within the reaction chamber 230. Where the sterilization chamber 205 is present and separate from the reaction chamber 230, the UV light produced by the UV light source 243 may still help to eliminate any microbes present in the hydroxyl ions and/or conveying gas.

The sterilization system 200 may have several advantages for deactivating or destroying contaminants. While the hydroxyl ions may be the predominant sterilizing agent, each of the components in the sterilization system 200 may be capable of deactivating and destroying contaminants. Hydroxyl radicals, hydrogen peroxide, UV light, and even titanium dioxide are used in other sterilization processes, and may help to sterilize the article 204 independently of the use of hydroxyl ions. The sterilization system 200 is relatively simple, and the various components that make up the sterilization system 200 are relatively inexpensive and easy to fabricate or obtain. Use of anhydrous hydrogen peroxide may expedite sterilization of the article 204 and/or reduce the amount of material (for example, the peroxide complex 208 and/or the photo initiator 241). Sterilization may be quick and reliable. The ability to locate the sterilization chamber 205 remote from the remainder of the sterilization system 200 may beneficially facilitate performance of local sterilization, avoiding or reducing the need to ship instruments to specialized facilities for sterilization.

The sterilization system 200 has been tested using biological indicators to represent contaminating microorganisms. Tests were run comparing the effectiveness of UV light sterilization compared to the use of hydrogen peroxide gas and then to the process of using the sterilization system 200. UV light in the 254 nm wavelength was used. There is evidence of the effectiveness of the 254 nm wavelength being an effective sterilization tool at least against certain bacteria and viruses. The hydrogen peroxide gas was present in a vaporized aqueous solution. There were three different strains of bacterial contaminants. The results are shown in a table 300 in FIG. 3.

As can be seen in the table 300, the use of the sterilization system 200 was the most effective and the quickest. UV light alone does not kill all of the bacterial strains. The hydrogen peroxide gas killed all the bacteria and did so in about 5 minutes. The use of the sterilization system 200, including production of anhydrous hydrogen peroxide with hydroxyl radicals to produce hydroxyl ions, was completely effective and took the least amount of time.

In some embodiments, the hydroxyl ions are used to sterilize a system for transporting biological substances, including the filling apparatus and at least a portion of the vessels used for transport. A sterilization system such as that described previously may be used to supply the hydroxyl ions. An exemplary filling system, or filling system 400, is shown and described in connection with FIG. 4.

Figure 4:
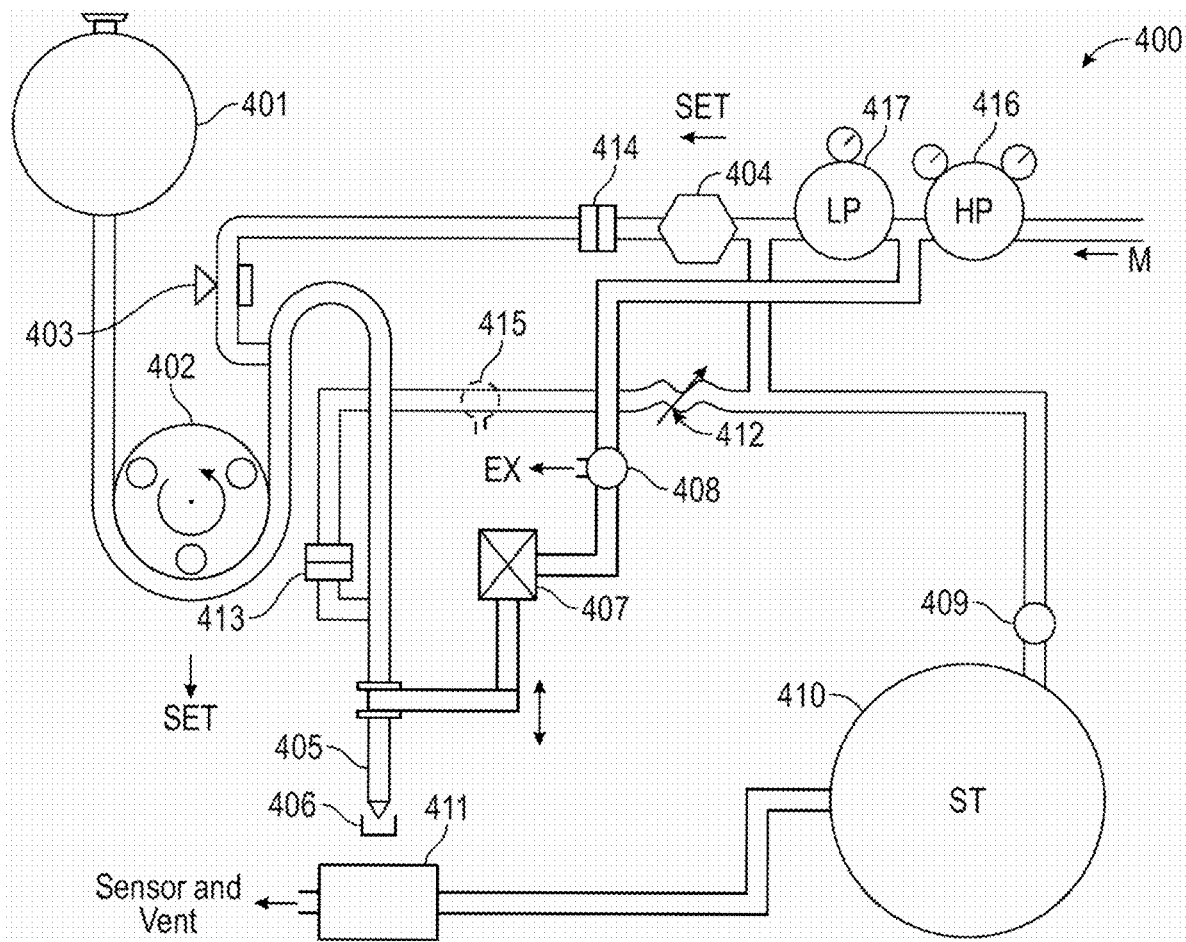
FIG. 4 is a schematic view of a sterilant filling system according to one embodiment.

Referring to FIG. 4, the filling system 400 may include a fluid media filter 401, a roller pump 402, a pinch valve 403, a sterilizing nitrogen filter 404, a fill tube 405, a fill tube cap 406, an actuator 407, a five-way spool valve 408, a solenoid valve 409, a sterilizing gas generator 410, a fill valve body 411, a flow restrictor valve 412, a CPC Sterile Connecter 413, a CPC Sterile connecter 414, a solenoid valve 415, a high-pressure nitrogen regulator 416, and a low-pressure nitrogen regulator 417.

The sterilization process may be used for sterilizing the filling apparatus which is used to fill a biological transport container such as the vessel 209 of FIG. 2. The filling sequence may proceed as follows:

1. Prepare the system by getting the load set;
2. Turn on the transport system, which may use a sealed nitrogen tank to supply the transport gas;
3. Remove the protective shipping cover from the fill valve so that the fill valve can connect to the container;
4. Begin the production of the sterilization compounds by heating the Carbamide Peroxide in the reaction chamber;
5. Load the bag fill port to the port lifter;
6. Raise the fill port;
7. Initiate the production of sterilizing gas by activating the UV light source and bombarding the photoinitator, titanium dioxide, with UV light to produce hydroxyl radicals, and transport the hydrogen peroxide gas to the reaction chamber;
8. Open the sterilization valve and open the exhaust valve to induce flow;
9. Close the exhaust valve is closed;
10. Initiate a timed sterilant exposure to produce the correct amount of sterilant;
11. Close the sterilization valve;
12. Open the exhaust valve again;
13. Open the nitrogen flush valve;

14. Close the exhaust and nitrogen valve;
15. Lower the fill valve to pierce the bag port top membrane and connect the fill tube to the empty bag;
16. Fill to the desired volume by cycling the roller pump;
17. Once the bag is filled, use a short burst of nitrogen to clear the bag port and tubing of liquid to eliminating dripping;
18. Seal the bag fill tube closed; and
19. Retract the filler fill tube.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A sterilization system for sterilizing an article, the sterilization system comprising:
   a hydrogen peroxide generation system configured to generate hydrogen peroxide;
   a hydroxyl radical generation system configured to produce a flow of hydroxyl radicals that causes deterioration of the hydrogen peroxide to produce hydroxyl ions; and
   a sterilization chamber configured to expose the article to the hydroxyl ions to sterilize the article;
   wherein the sterilization chamber is separate from the hydroxyl radical generation system.

2. The sterilization system of claim 1, wherein:
   the hydrogen peroxide generation system comprises a first chamber configured to receive a peroxide complex configured to release hydrogen peroxide gas; and
   the sterilization system further comprises a reaction chamber comprising the hydroxyl radical generation system.

3. The sterilization system of claim 2, wherein:
   the reaction chamber is configured to receive the hydrogen peroxide generated by the hydrogen peroxide generation system; and
   the hydroxyl radicals react with the hydrogen peroxide within the reaction chamber.

4. The sterilization system of claim 1, further comprising a gas transport system configured to urge the hydroxyl ions from the hydroxyl radical generation system into the sterilization chamber by urging a second gas under pressure through the sterilization system.

5. The sterilization system of claim 4, wherein the second gas is non-reactive with the hydrogen peroxide, the hydroxyl radicals, and the hydroxyl ions.

* * * * *